US009393236B2

(12) United States Patent
Delay-Goyet et al.

(10) Patent No.: US 9,393,236 B2
(45) Date of Patent: Jul. 19, 2016

(54) USE OF 4-CYCLOPROPYLMETHOXY-N-(3,5-DICHLORO-1-OXIDO-4-PYRIDIN-4-YL)-5-(METHOXY)PYRIDINE-2-CARBOXAMIDE IN THE TREATMENT OF CRANIAL TRAUMAS

(75) Inventors: Philippe Delay-Goyet, Paris (FR); Corinne Perron, Paris (FR)

(73) Assignee: SANOFI, Paris (FR)

( * ) Notice: Subject to any disclaimer, the term of this patent is extended or adjusted under 35 U.S.C. 154(b) by 68 days.

(21) Appl. No.: 12/573,322

(22) Filed: Oct. 5, 2009

(65) Prior Publication Data
US 2010/0130553 A1 May 27, 2010

Related U.S. Application Data

(63) Continuation of application No. PCT/FR2008/000531, filed on Apr. 16, 2008.

(30) Foreign Application Priority Data

Apr. 19, 2007 (FR) ..................................... 07 02852

(51) Int. Cl.
  *A01N 43/40* (2006.01)
  *A61K 31/435* (2006.01)
  *A61K 31/44* (2006.01)
  *A61K 31/444* (2006.01)
(52) U.S. Cl.
  CPC .................................. *A61K 31/444* (2013.01)
(58) Field of Classification Search
  USPC ......................................................... 514/277
  See application file for complete search history.

(56) References Cited

U.S. PATENT DOCUMENTS

| 4,193,926 | A | 3/1980 | Schmiechen et al. | |
| 6,177,077 | B1 | 1/2001 | Tobinick et al. | |
| 6,472,412 | B1 * | 10/2002 | Fenton et al. | 514/348 |
| 7,045,660 | B2 | 5/2006 | Fenton et al. | |
| 7,652,144 | B2 | 1/2010 | Fenton et al. | |
| 8,129,537 | B2 | 3/2012 | Fenton et al. | |
| 8,592,443 | B2 | 11/2013 | Delay-Goyet et al. | |
| 2003/0069169 | A1 | 4/2003 | Macor et al. | |
| 2007/0021451 | A1 | 1/2007 | Kazui et al. | |

FOREIGN PATENT DOCUMENTS

| GB | 2406856 | 4/2005 |
| JP | 2003519139 | 6/2003 |
| JP | 2005506286 | 3/2005 |
| WO | WO95/04045 | 2/1995 |
| WO | WO 95/20578 | 8/1995 |
| WO | WO 96/31476 | 10/1996 |
| WO | WO 0075116 A2 * | 12/2000 |
| WO | WO 01/47915 | 7/2001 |
| WO | WO 02/069905 | 9/2002 |
| WO | WO 2004/005258 | 1/2004 |
| WO | WO 2004/067006 | 8/2004 |
| WO | WO 2006/135828 | 12/2006 |

OTHER PUBLICATIONS

U.S. Appl. No. 12/573,316, filed Oct. 5, 2009, Delay-Goyet, et al.
U.S. Appl. No. 12/573,326, filed Oct. 5, 2009, Delay-Goyet, et al.
U.S. Appl. No. 12/573,326—Office Action Dated Jul. 23, 2010.
Barneoud, P., et al., Quantitative Motor Assessment in Fals Mice: A Longitudinal Study, Neuroreport, vol. 8, pp. 2861-2885, (1997).
Berk, C., et al., Thalamic Deep Brain Stimulation for the Treatment of Tremor Due to Multiple Sclerosis: A Prospective Study of Tremor and Quality of Life, J. Neurosurg, vol. 97, pp. 815-820, (2002).
Menniti, et al., Phosphodiesterases in the CNS: Targets for Drug Development, Nature Reviews, vol. 5, (2006), pp. 660-670.
Nikulina, E., et al., The Phosphodiesterase Inhibitor Rolipram Delivered After Spinal Cord Lesion Promotes Axonal Regeneration and Functional Recovery, Proceedings of the National Academy of Sciences of the United States of America, vol. 101, No. 23, pp. 8786-8790, Jun. 8, 2004.
Robichaud, et al., Emesis Induced by Inhibitors of Type IV Cyclic Nucleotide Phosphodiesterase (PDE IV) in the Ferret, Neuropharmacology, vol. 38, (1999), pp. 289-297.
U.S. Appl. No. 12/573,316—Office Action Dated Feb. 15, 2011.
U.S. Appl. No. 12/573,326—Office Action Dated Dec. 10, 2010.
Houslay, et al., Phosphodiesterase-4 as a Therpaeutic Target, DDT, vol. 10, No. 22, (2005), pp. 1503-1519.
Sawanishi, et al., Selective Inhibitors of Cyclic AMP-Specific Phosphodiesterase: Heterocycle-Condensed Purines, J. Med. Chem., (1997), vol. 40, pp. 3248-3253.
He, et al., Novel Cyclic Compounds as Potent Phosphodiesterase 4 Inhibitors, J. Med. Chem., vol. 41, pp. 4216-4223, (1998).
Burnouf, et al., Synthesis, Structure-Activity Relationships, and Pharmacological Profile of 9-Amino-4-oxo-1-phenyl-3,4,6,7-tetrahydro[1,4]diazepino[6,7,1-hi]indoles: Discovery of Potent, Selective Phosphodiesterase Type 4 Inhibitors, J. Med. Chem., (2000), vol. 43, pp. 4850-4867.
Aoki, et al., Effect of a Novel Anti-Inflammatory Compound, YM976, on Antigen-Induced Eosinophil Infiltration into the Lungs in Rats, Mice, and Ferrets, The Journal of Pharmacology and Experimental Therapeutics, (2000), vol. 295, No. 3, pp. 1149-1155.
International Search Report for WO2008/145838 dated Dec. 4, 2008.
Arvin, et al., Brain Injury and Inflammation A Putative Role of TNFa, Annals of the New York Academy of Sciences, vol. 765, No. 1, pp. 62-71, (1995).
Kambayashi, et al., Cyclic Nucleotide Phosphodiestrerase Type IV Participates in the Regulation of IL-10 in the Subsequent Inhibition of TNF-a and II-6 Release by Endotoxin-Stimulated Macrophages, The Journal of Immunology, vol. 155, No. 10, pp. 4909-4916, (1995).
Atkins, C.M. et al. (Jan. 4, 2013). "Effects of Rolipram on Histopathological Outcome After Controlled Cortical Impact Injury in Mice," *Neurosci. Letters* 532:1-6.
Atkins, C.M. et al. (Sep. 2012). "Post-Injury Treatment with Rolipram Increases Hemorrhage after Traumatic Brain Injury," *J. Neurosci. Res.* 90(9):1861-1871.
Block, F. et al. (Dec. 1, 1997). "Delayed Treatment with Rolipram Protects Against Neuronal Damage Following Global Ischemia in Rats," *Neuroreport.* 8(17):3829-3832 (Abstract Only).

(Continued)

*Primary Examiner* — Layla Soroush
(74) *Attorney, Agent, or Firm* — Morrison & Foerster LLP

(57) ABSTRACT

The invention relates to the use of 4-cyclopropylmethoxy-N-(3,5-dichloro-1-oxidopyridin-4-yl)-5-(methoxy)pyridine-2-carboxamide for the preparation of a medicament for use in the treatment of cerebral traumas.

4 Claims, No Drawings

(56) References Cited

OTHER PUBLICATIONS

Columbia University Medical Center. (2015). "Department of Neurological Surgery—Cerebral Ischemia," located at <http://www.columbianeurosurgery.org/conditions/cerebral-ischemia/>, last visited on Jul. 1, 2015, three pages.

Dixon, C.E. et al. (Feb. 1998). "Protective Effects of Moderate Hypothermia on Behavioral Deficits but not Necrotic Cavitation Following Cortical Impact Injury in the Rat," *J. Neurotrauma* 15(2):95-103.

Goldberg, S.A. et al. (2015). "The Prehospital Management of Traumatic Brain Injury," Chapter 23 in *Handbook of Clinical Neurology*, vol. 127 (3$^{rd}$ Series) Traumatic Brain Injury, Part I, Elsevier B.V., pp. 367-378.

Kato, H. et al. (Jan. 5, 1995). "Rolipram, a Cyclic AMP-Selective Phosphodiesterase Inhibitor, Reduces Neuronal Damage Following Cerebral Ischemia in the Gerbil," *Eur. J. Pharmacol.* 272(1):107-110 (Abstract Only).

Kushner, D.S. et al. (Aug. 2014). "Dual Diagnosis: Traumatic Brain Injury with Spinal Cord Injury," *Phys. Med. Rehabil. Clin. N. Am.* 25(3):681-696.

Michel, P. (2009). "General Principles of Acute Stroke Management," Chapter 56 in *Handbook of Clinical Neurology*, vol. 94 (3$^{rd}$ Series) Stroke, Part III, Elsevier B.V., pp. 1129-1154.

Nih (2014). "How is a Stroke Treated," located at http://www.nhlbi.nih.gov/health/health-topics/topics/stroke/treatment#>, last visited on Jul. 1, 2015, two pages.

Nih (2015). "NINDS Traumatic Brain Injury Information Page," located at http://www.ninds.nih.gov/disorders/tbi/tbi.htm#Is_there_any_treatment>, last visited on Jul. 1, 2015, four pages.

Nih (2015). "NINDS Spinal Cord Injury Information Page," located at <http://www.ninds.nih.gov/disorders/sci/sci.htm>, last visited on Jul. 1, 2015, four pages.

Titus, D.J. et al. (2014). "Phosphodiesterase Inhibitors as Therapeutics for Traumatic Brain Injury," *Curr. Pharm. Des.* 21(3):332-342.

Zhang, B. et al. (2014). "Is Neuroinflammation in the Injured Spinal Cord Different Than in the Brain? Examining Intrinsic Differences Between the Brain and Spinal Cord," *Exp. Neurology* 258:112-120.

\* cited by examiner

USE OF 4-CYCLOPROPYLMETHOXY-*N*-(3,5-DICHLORO-1-OXIDO-4-PYRIDIN-4-YL)-5-(METHOXY)PYRIDINE-2-CARBOXAMIDE IN THE TREATMENT OF CRANIAL TRAUMAS

This application is a Continuation of International Application No. PCT/FR2008/000531, filed Apr. 16, 2008, which is incorporated herein by reference in its entirety.

The present invention relates to the use of 4-cyclopropylmethoxy-N-(3,5-dichloro-1-oxidopyridin-4-yl)-5-(methoxy)pyridine-2-carboxamide, in the form of a hydrate, of a solvate, of a base or of an addition salt with an acid, for the preparation of a medicament for use in the treatment of cerebral traumas.

4-Cyclopropylmethoxy-N-(3,5-dichloro-1-oxidopyridin-4-yl)-5-(methoxy)pyridine-2-carboxamide, or alternatively called N-(3,5-dichloro-1-oxido-4-pyridinio)-4-cyclopropylmethoxy-5-methoxypyridine-2-carboxamide, is known to be part of the composition of medicaments for use in the treatment of various pathologies, including in particular inflammations of the joints, arthritis and rheumatoid arthritis. This compound, in hemihydrate form, is described, for example, in document WO95/04045 (compound referenced FR).

There exists a need to find medicaments for treating patients suffering from cerebral traumas. Studies have shown, in animals, that a possible approach is the administration of compounds which inhibit phosphodiesterases 4 (PDE 4), such as, for example rolipram. However, clinical studies have shown that this compound, and also other inhibitors of PDE 4, induce emetic effects which do not allow it to be used in therapy.

It has now been found that 4-cyclopropylmethoxy-N-(3,5-dichloro-1-oxidopyridin-4-yl)-5-(methoxy)pyridine-2-carboxamide can be used in the treatment of cerebral traumas, while at the same time avoiding the emetic effects at therapeutically acceptable doses.

A first subject of the invention therefore relates to the use of 4-cyclopropyl methoxy-N-(3,5-dichloro-1-oxidopyridin-4-yl)-5-(methoxy)pyridine-2-carboxamide for the preparation of a medicament for use in the treatment of cerebral traumas.

According to one embodiment of the invention, the use of 4-cyclopropylmethoxy-N-(3,5-dichloro-1-oxidopyridin-4-yl)-5-(methoxy)pyridine-2-carboxamide can be carried out with the latter in the form of a base or of an addition salt with an acid.

The salts that can be used in the context of the invention can be prepared with pharmaceutically acceptable acids, but the salts of other acids that are useful, for example, for the purification or the isolation of 4-cyclopropylmethoxy-N-(3,5-dichloro-1-oxidopyridin-4-yl)-5-(methoxy)pyridine-2-carboxamide are also part of the invention.

The use of 4-cyclopropylmethoxy-N-(3,5-dichloro-1-oxidopyridin-4-yl)-5-(methoxy)pyridine-2-carboxamide according to the invention can also be carried out with the latter in the form of a hydrate or of a solvate. The term "hydrate or solvate" is intended to mean the association or the combination of one or more molecules of 4-cyclopropylmethoxy-N-(3,5-dichloro-1-oxidopyridin-4-yl)-5-(methoxy)pyridine-2-carboxamide with one or more molecules of water or of solvent.

For the purpose of the present invention, the term "cerebral traumas" is intended to mean traumas of external origin, such as, for example, cranial traumas caused in particular by an impact, a road accident, a fall or crushing.

A second subject of the invention relates to a pharmaceutical composition comprising 4-cyclopropylmethoxy-N-(3,5-dichloro-1-oxidopyridin-4-yl)-5-(methoxy)pyridine-2-carboxamide as active ingredient, and one or more pharmaceutically acceptable excipients.

The composition used according to the invention comprises an effective dose of the active ingredient.

For example, the daily doses of active ingredient that can be used according to the invention are from 0.001 to 10 mg/day.

According to the usual practice, the dosage appropriate for each patient is determined by the physician according to the method of administration and the age, weight and response of said patient.

The doses depend on the desired effect, on the duration of treatment and on the route of administration used.

There may be specific cases where higher or lower dosages are appropriate. Such dosages do not depart from the context of the invention.

The excipients are chosen, according to the pharmaceutical form and the method of administration desired, from the usual excipients which are known to those skilled in the art.

The composition may be administered orally, parenterally or rectally.

The appropriate unit administration forms comprise oral administration forms, such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular, intravenous or intrathecal administration forms, rectal administration forms, and implants. For topical application, the active ingredients according to the invention may be used in creams, gels, ointments or lotions.

When a composition is prepared in tablet form, the active ingredient is mixed with one or more pharmaceutical excipients, such as gelatin, starch, lactose, magnesium stearate, talc, silica, gum arabic, mannitol, microcrystalline cellulose, hypromellose or the like.

The tablets may be coated with sucrose, with a cellulosic derivative or with other substances suitable for coating. The tablets may be produced by various techniques, such as direct compression, dry or wet granulation, or hot melt.

It is also possible to obtain a pharmaceutical composition in the form of a gel capsule by mixing the active ingredient with a diluent and transferring the mixture obtained into soft or gel capsules.

For parenteral administration, use is made of aqueous suspensions, isotonic saline solutions or sterile injectable solutions which contain pharmacologically compatible agents, for example propylene glycol or butylene glycol.

By way of example, a unit administration form of 4-cyclopropylmethoxy-N-(3,5-dichloro-1-oxidopyridin-4-yl)-5-(methoxy)pyridine-2-carboxamide in tablet form comprises the following ingredients:

| | |
|---|---|
| 4-Cyclopropylmethoxy-N-(3,5-dichloro-1-oxidopyridin-4-yl)-5-(methoxy)pyridine-2-carboxamide | 1 mg |
| Mannitol | 224 mg |
| Sodium croscarmellose | 5 mg |
| Maize starch | 15 mg |
| Hydroxypropylmethylcellulose | 2 mg |
| Magnesium stearate | 3 mg |

The effects of 4-cyclopropylmethoxy-N-(3,5-dichloro-1-oxidopyridin-4-yl)-5-(methoxy)pyridine-2-carboxamide used according to the invention were evaluated in a cranial trauma model.

EXPERIMENT 1

Effect of Chronic Treatment with the Compound of the Invention in the CFR (Conditioned Freezing Response) Test after a Parietal Cranial Trauma After general anaesthesia, rats (Sprague-Dawley, male, 150-200 g, Charles River) are placed in a stereotaxis frame. A craniotomy is performed at the level of the parietal cortex (AP: 3.5 mm; LAT: 7 mm and 3.5 mm below the cranial roof). A catheter connected to an HPLC pump is placed in contact with the dura mater and a pressure of 0.073 Kpsi is exerted.

The animals are treated intravenously 4 h after the surgery (D0) by administering a solution of 4-cyclopropylmethoxy-N-(3,5-dichloro-1-oxidopyridin-4-yl)-5-(methoxy)pyridine-2-carboxamide in the carrier (PEG200/physiological saline (NaCl 0.9%)), at the dose of 0.05 mg/kg.

Starting from D1 and up to D21 post-surgery, the animals are treated with a solution containing 4-cyclopropylmethoxy-N-(3,5-dichloro-1-oxidopyridin-4-yl)-5-(methoxy)pyridine-2-carboxamide in the carrier (methylcellulose (MC) (0.6%)+tween-80 (0.5%) in water) per os, twice a day, at the total daily dose of 0.1 mg/kg.

The deficiency in the CFR was measured at days D23 and D24 post-surgery.

At D23, the animal is placed in a box, where it receives an electric shock of 0.6 mA for 1.5 s.

At D24, the animal is again placed in the same box and the duration of immobility is measured for 3 minutes.

A lesion induced by a trauma of the parietal cortex significantly reduces the immobility time.

The treatment with 4-cyclopropylmethoxy-N-(3,5-dichloro-1-oxidopyridin-4-yl)-5-(methoxy)pyridine-2-carboxamide at the dose of 0.1 mg/kg/day produces 100% inhibition of the deficiency induced by a cranial trauma ($p<0.001$ in comparison with the traumatized animal given the carrier).

EXPERIMENT 2

Evaluation of the Emetic Effects of 4-cyclopropylmethoxy-N-(3,5-dichloro-1-oxidopyridin-4-yl)-5-(methoxy)pyridine-2-carboxamide The emetic capacity of 4-cyclopropylmethoxy-N-(3,5-dichloro-1-oxidopyridin-4-yl)-5-(methoxy)pyridine-2-carboxamide was evaluated in the ferret. Two groups of ferrets were used, the first receiving the carrier (PEG200) and the second receiving 4-cyclopropyl methoxy-N-(3,5-dichloro-1-oxidopyridin-4-yl)-5-(methoxy)pyridine-2-carboxamide in solution in the carrier (PEG 200), by oral gavage. The animals were observed continually for the 2 hours following the administration, and then every hour up to 6 hours after the administration. The clinical signs (in particular retching and vomiting) were noted.

When administered at 0.1 mg/kg, 4-cyclopropylmethoxy-N-(3,5-dichloro-1-oxidopyridin-4-yl)-5-(methoxy)pyridine-2-carboxamide induces no retching or vomiting in the 5 ferrets treated.

These results show that the administration of a therapeutic dose of 4-cyclopropylmethoxy-N-(3,5-dichloro-1-oxidopyridin-4-yl)-5-(methoxy)pyridine-2-carboxamide for treating cerebral traumas does not cause any emetic effect.

EXAMPLE 3

Evaluation of the Emetic Effects of (R)-(−)rolipram (((4R)-4-[3-(cyclopentyloxy)-4-methoxyphenyl]pyrrolidine-2-one))

The emetic capacity of (R)-(−)-rolipram was evaluated in the ferrets. Two groups of ferrets were used, the first being given the carrier (PEG200) and the second being given the (((4R)-4-[3-(cyclopentyloxy)-4-methoxyphenyl]pyrrolidine-2-one)) in solution in the carrier (PEG 200), by oral gavage, at doses of 0.05 mg/kg and of 0.1 mg/kg. The animals were observed continually for the 2 hours following administration, and then once an hour up to 6 hours after the administration. The clinical signs were noted.

When administered at 0.05 mg/kg and 0.1 mg/kg, (R)-(−)-rolipram induces vomiting in the ferrets treated.

The results of example 3 show that the administration of a therapeutic dose of (R)-(−)-rolipram causes any emetic effects.

Thus, 4-cyclopropylmethoxy-N-(3,5-dichloro-1-oxidopyridin-4-yl)-5-(methoxy)pyridine-2-carboxamide is of use in the preparation of a medicament for the treatment of cerebral traumas, such as, for example, traumas occurring during a fall, an impact or a car accident, while at the same time avoiding possible emetic effects at acceptable therapeutic doses.

We claim:

1. A method for treating cerebral trauma of external origin comprising administering to a patient in need thereof a pharmaceutically effective amount of 4-cyclopropylmethoxy-N-(3,5-dichloro-1-oxidopyridin-4-yl)-5-(methoxy)pyridine-2-carboxamide, or a hemihydrate, or an addition salt with an acid thereof, wherein the treatment does not cause an emetic effect or induce retching or vomiting to the patient.

2. A method for treating cerebral trauma of external origin comprising administering to a patient in need thereof a pharmaceutically effective amount of 4-cyclopropylmethoxy-N-(3,5-dichloro-1-oxidopyridin-4-yl)-5-(methoxy)pyridine-2-carboxamide, wherein the treatment does not cause an emetic effect or induce retching or vomiting to the patient.

3. The method according to claim 1, wherein 4-cyclopropylmethoxy-N-(3,5-dichloro-1-oxidopyridin-4-yl)-5-(methoxy)pyridine-2-carboxamide is administered at the dose 0.001 to 10 mg/day.

4. The method according to claim 2, wherein 4-cyclopropylmethoxy-N-(3,5-dichloro-1-oxidopyridin-4-yl)-5-(methoxy)pyridine-2-carboxamide is administered at the dose 0.001 to 10 mg/day.

* * * * *